United States Patent
Tegg

(10) Patent No.: US 9,861,433 B2
(45) Date of Patent: Jan. 9, 2018

(54) HELICAL-SHAPED ABLATION CATHETER AND METHODS OF USE

(71) Applicant: St. Jude Medical, Cardiology Division, Inc., St. Paul, MN (US)

(72) Inventor: Troy Tegg, Elk River, MN (US)

(73) Assignee: ST. JUDE MEDICAL, CARDIOLOGY DIVISION, INC., St. Paul, MN (US)

(*) Notice: Subject to any disclaimer, the term of this patent is extended or adjusted under 35 U.S.C. 154(b) by 645 days.

(21) Appl. No.: 14/515,574

(22) Filed: Oct. 16, 2014

(65) Prior Publication Data

US 2015/0126996 A1 May 7, 2015

Related U.S. Application Data

(60) Provisional application No. 61/899,944, filed on Nov. 5, 2013.

(51) Int. Cl.
*A61B 18/14* (2006.01)
*A61M 25/00* (2006.01)
(Continued)

(52) U.S. Cl.
CPC ..... *A61B 18/1492* (2013.01); *A61M 25/0012* (2013.01); *A61M 25/0141* (2013.01);
(Continued)

(58) Field of Classification Search
CPC ...... A61B 18/1492; A61B 2017/00323; A61B 2017/00526; A61B 2017/00867; A61B 2017/00955; A61B 2018/00267; A61B 2018/00404; A61B 2018/00577; A61B 2018/00952; A61B 2018/1435;
(Continued)

(56) References Cited

U.S. PATENT DOCUMENTS 3,650,277 A 3/1972 Sjostrand et al.
4,658,819 A 4/1987 Harris et al.
(Continued)

FOREIGN PATENT DOCUMENTS

WO 97/45157 12/1997
WO 00/66020 11/2000
(Continued)

OTHER PUBLICATIONS

Dibona, Gerald F., Renal Innervation and Denervation: Lessons from Renal Transplantation Reconsidered, Artificial Organs, vol. 11, No. 6, 1987, 457-462.
(Continued)

*Primary Examiner* — Jaymi Della
(74) *Attorney, Agent, or Firm* — Armstrong Teasdale LLP

(57) ABSTRACT

The present disclosure provides ablation catheters that are constructed such that they may be inserted into the body and into a target blood vessel in a linear conformation and subsequently changed into a helical conformation using a pull wire secured to the ablation catheter prior to an ablation procedure to allow electrodes present on the ablation catheter to contact the wall of the blood vessel. After the ablation is complete, the helical-shaped ablation catheter may be returned to its linear conformation by reversing the tensioned pull wire for extraction from the body.

18 Claims, 6 Drawing Sheets

(51) Int. Cl.
*A61M 25/01* (2006.01)
*A61B 18/00* (2006.01)
*A61B 17/00* (2006.01)

(52) U.S. Cl.
CPC .............. *A61B 2017/00323* (2013.01); *A61B 2017/00526* (2013.01); *A61B 2017/00867* (2013.01); *A61B 2017/00955* (2013.01); *A61B 2018/00267* (2013.01); *A61B 2018/00404* (2013.01); *A61B 2018/00577* (2013.01); *A61B 2018/00952* (2013.01); *A61B 2018/1435* (2013.01); *A61M 25/001* (2013.01); *A61M 25/0147* (2013.01); *A61M 2025/015* (2013.01); *Y10T 29/49002* (2015.01)

(58) Field of Classification Search
CPC .......... A61M 25/0012; A61M 25/0141; A61M 25/001; A61M 25/0147; A61M 2025/015; A61M 25/0052; A61M 25/0053; Y10T 29/49002
See application file for complete search history.

(56) References Cited

U.S. PATENT DOCUMENTS

| | | |
|---|---|---|
| 5,035,694 A | 7/1991 | Kasprzyk et al. |
| 5,239,999 A * | 8/1993 | Imran .................. A61B 5/0422 600/374 |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Muller et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Muller et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2001/0020174 A1* | 9/2001 | Koblish ............. A61B 18/1492 606/194 |
| 2002/0004631 A1* | 1/2002 | Jenkins ............. A61B 18/1492 600/374 |
| 2002/0068885 A1 | 6/2002 | Harhen et al. |
| 2002/0111618 A1* | 8/2002 | Stewart ............. A61B 18/1492 606/41 |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem et al. |
| 2006/0089678 A1 | 4/2006 | Shalev |
| 2007/0129720 A1* | 6/2007 | Demarais ............. A61N 1/0551 606/41 |
| 2007/0135875 A1 | 6/2007 | Demarais et al. |
| 2008/0172084 A1* | 7/2008 | Kusleika .................. A61F 2/01 606/201 |
| 2008/0255478 A1 | 10/2008 | Burdette |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |

(56) References Cited

FOREIGN PATENT DOCUMENTS

| WO | 2007/149970 | 12/2007 |
|---|---|---|
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of the American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.
Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, A. Neil et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.

(56) References Cited

OTHER PUBLICATIONS

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, JR, Joseph L. et al, The Sympathetic Nervous System and Baroreflexes in Hypertension and Hypotension, Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL:http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

(56) References Cited

OTHER PUBLICATIONS

Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.nriedtronic.com, Jan. 9, 2014.
Medtronic, Inc., RDN Therapy with the Symplicity Renal Denervation System, Procedure Fact Sheet, www. medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65,729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II,II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

(56) References Cited

OTHER PUBLICATIONS

Page, Max, Section of Surgery, Discussion on the Surgical Treatment of Hypertension, Proceedings of the Royal Society of Medicine, vol. XLI, Feb. 1948, 359-372.

Papademetriou, Vasilios, Hypertension and the Simplicity Renal Denervation System, Scientific Background, www.medtronic.com, 2011.

Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3):139-142.

Persu, Alexandre et al, Renal Denervation: Ultima Ratio or Standard in Treatment-Resistant Hypertension, Hypertension Journal of The American Heart Association, Sep. 2012;60(3):596-606.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4: 1886-1891, 2009.

Zazgornik, Jan et al, Bilateral Nephrectomy: The Best, but Often Overlooked, Treatment for Refractory Hypertension in Hemodialysis Patients, AJH 1998; 11:1364-1370.

Robbins, Ivan M. et al, Pulmonary Vein Stenosis After Catheter Ablation of Atrial Fibrillation, Circulation Journal of The American Heart Association, 1998;98:1769-1775.

Rocha-Singh, Krishna J., Catheter-Based Sympathetic Renal Denervation a Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of The American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept, Hypertension Journal of The American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of The American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

(56) References Cited

OTHER PUBLICATIONS

Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.

Young, Robert R. et al, Reversible Block of Nerve Conduction by Ultrasound Ultrasonic Blocking of Nerve Fibers, Arch Neurol. 1961;4(1):83-89.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

(56) References Cited

OTHER PUBLICATIONS

Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part II, 621-624.

\* cited by examiner

HELICAL-SHAPED ABLATION CATHETER AND METHODS OF USE

CROSS-REFERENCE TO RELATED APPLICATIONS

This application claims priority to provisional application Ser. No. 61/899,944, filed Nov. 5, 2013, the entire specification of which is incorporated herein.

A. Field of the Disclosure

The present disclosure relates generally to a catheter system for use in a human body, and more particularly to an ablation catheter configured to form a helical conformation after insertion into a body and prior to use in an ablation procedure.

B. Background Art

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient. The catheter typically carries one or more working components, such as electrodes and thermocouples, or other diagnostic, therapeutic or ablative devices for carrying out the procedures. One or more controls or actuators may be provided on the handle for selectively adjusting one or more characteristics of the working components.

One particular example of a multi-electrode catheter system is an ablative catheter system in which the working component is a multi-electrode assembly carried at the distal end of a flexible catheter. A control wire generally extends within the catheter from the multi-electrode assembly to the handle to operatively connect the multi-electrode assembly to an actuator on the handle. Manipulating the actuator acts on the control wire to configure the multi-electrode assembly into a desired configuration for carrying out the ablative procedure. For example, in one such ablative catheter system made by St. Jude Medical, Inc. under the trade name EnligHTN, the multi-electrode assembly is an electrode assembly in the general form of an electrode basket. The electrode basket generally includes a number of Nitinol struts, wherein each strut may include one or two electrodes. The electrode basket is formed using the Nitinol struts in combination with an adhesive material that is used at certain points to hold the electrode basket together for use in an ablation procedure.

BRIEF SUMMARY OF THE DISCLOSURE

In one embodiment, the present disclosure is directed to an ablation catheter. The ablation catheter comprises a flexible catheter having a proximal end and a distal end, a pull wire fixedly attached along at least a portion of the circumference of the distal end of the flexible catheter to a pull ring such that the flexible catheter is capable of forming a helical configuration upon tensioning of the pull wire. The flexible catheter additionally comprises at least one electrode coupled to the flexible catheter at the distal end.

In another embodiment, the present disclosure is directed to a method of manufacturing an ablation catheter. The method comprises fixedly attaching a pull wire along at least a portion of a circumference of a distal end of a flexible catheter to a pull ring such that the flexible catheter is capable of forming a helical configuration upon tensioning of the pull wire and coupling at least one electrode to the flexible catheter at the distal end.

In another embodiment, the present disclosure is directed to a method of ablating tissue. The method comprises inserting a flexible catheter into a patient wherein the flexible catheter comprises a proximal end and a distal end, a pull wire fixedly attached along at least a portion of the circumference of the distal end of the flexible catheter to a pull ring such that the flexible catheter is capable of forming a helical configuration upon tensioning of the pull wire, and at least one electrode coupled to the flexible catheter at the distal end; providing tension to the pull wire such that the flexible catheter forms a helical shape; and providing energy to the at least one electrode.

In another embodiment, the present disclosure is directed to an ablation catheter. The ablation catheter comprises a flexible catheter configured to form a helical structure.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides ablation catheters that are configured such that they may be inserted into the body and into a target blood vessel in a linear conformation and subsequently changed into a helical conformation using a pull wire secured to the ablation catheter prior to an ablation procedure to allow one or more electrodes present on the ablation catheter to contact the wall of the blood vessel. After the ablation process is complete, the helical-shaped ablation catheter may be returned to its linear conformation by reversing the tensioned pull wire for extraction from the body. By configuring the catheter such that it can be formed into a helical conformation during an ablation procedure and subsequently returned to a linear conformation after the procedure, the present disclosure provides an ablation catheter that can utilize larger sized electrodes placed on the catheter for ablation procedures as the linear conformation allows such larger electrodes easier access to the body and blood vessel through small sized catheters. By using larger electrodes on the ablation catheter, the current density applied to the tissue being ablated may be reduced as the energy from the electrodes may be spaced out over a larger surface area of the vessel, which allows the tissue to better absorb the energy. By spreading the current density over a larger area of the artery, procedural outcomes may be improved and procedure times may be shortened.

In addition to the benefits of using larger electrodes on the ablation catheter as noted above, the ablation catheters described herein are configured to form a helical structure using a pull wire inside of a blood vessel and may be less complex to manufacture as the number of manufacturing steps is reduced as compared to conventional electrode baskets. The helical ablation catheters described herein may also provide improved durability and reliability.

Figure 1:
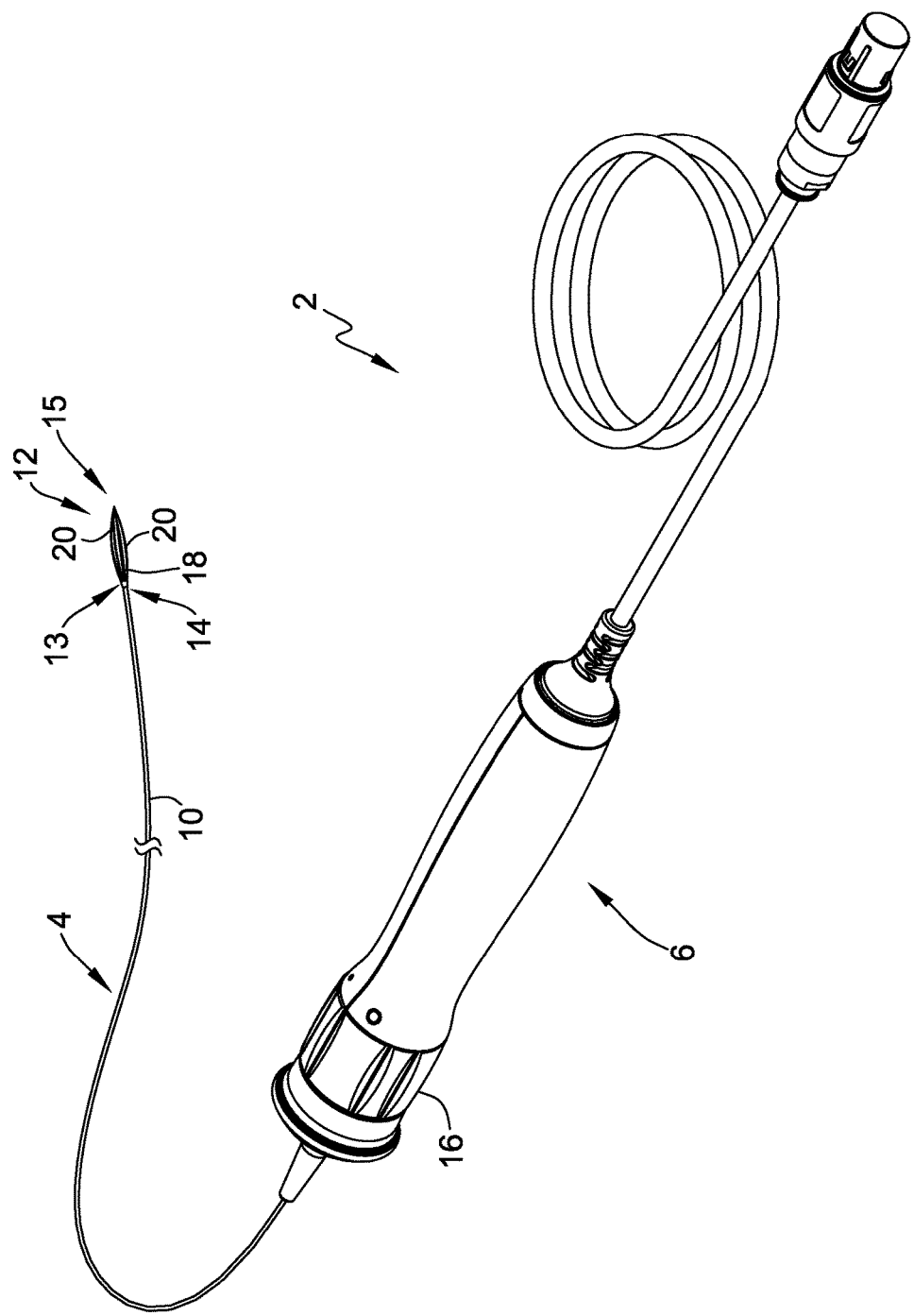
FIG. 1 is a perspective view of one embodiment of a catheter system including a handle, a catheter and an electrode assembly having multiple electrodes, with the electrode assembly being in a collapsed configuration.
Figure 2:
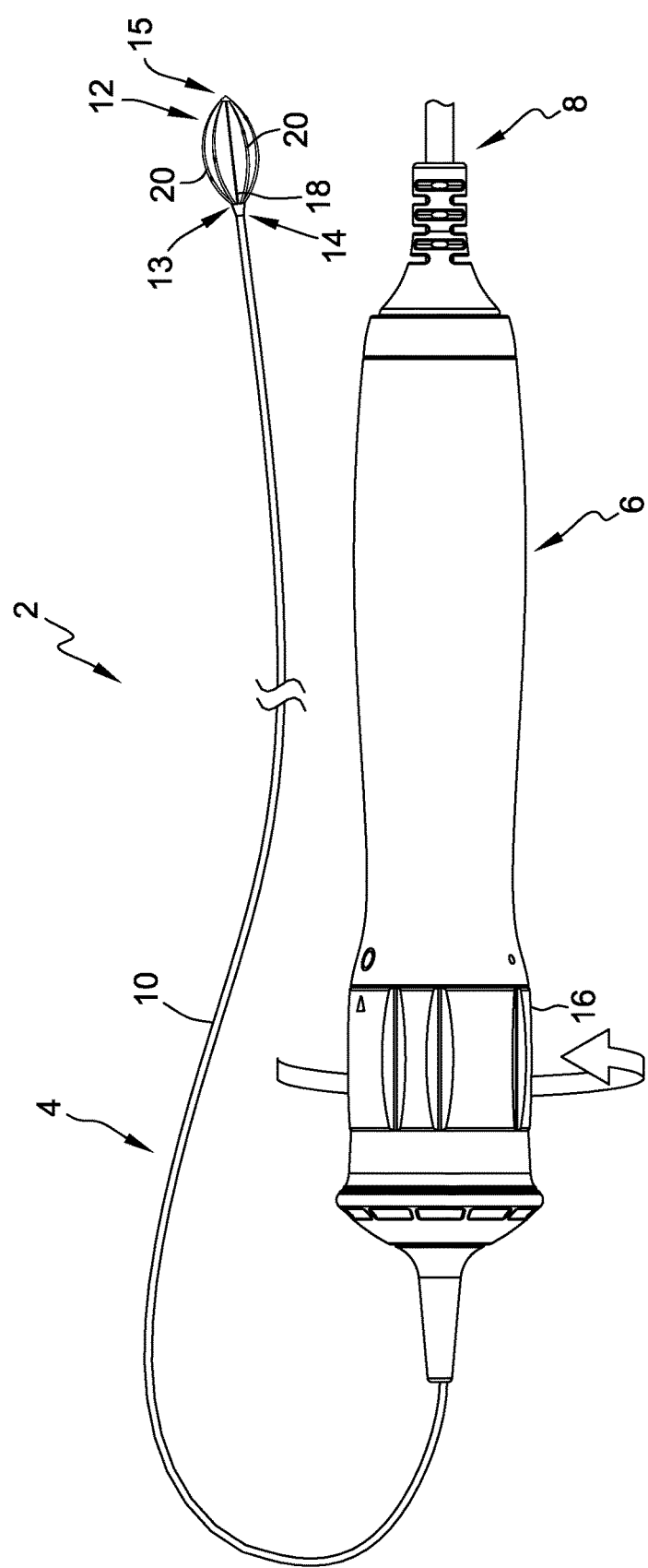
FIG. 2 is a side elevation of the catheter system of FIG. 1, with the electrode assembly being in an expanded configuration resulting from rotation of a rotatable actuator.

Referring now to the drawings, and in particular to FIGS. 1 and 2, a conventional catheter system 2 is shown by way of background and reference. Catheter system 2 includes a flexible catheter 4, a handle 6 to which flexible catheter 4 is connected, and a conductor assembly 8 for electrically connecting catheter system 2 to a suitable power supply (not shown). As one example, catheter system 2 illustrated and described herein is suitably constructed for use as an ablation system, such as a renal or heart ablation system. More particularly, illustrated catheter system 2 is a multi-electrode renal denervation system. One example of such a catheter system 2 is currently made by St. Jude Medical, Inc. under the trade name EnligHTN. General operation of a multi-electrode renal denervation system is known to those of skill in the art and is not described further herein except to the extent necessary to describe the present embodiments. It is also understood that catheter system 2 may be used for any other suitable treatment or purpose without departing from the scope of this disclosure. Additionally, while catheter system 2 is illustrated and described herein as including flexible catheter 4, catheter system 2 may further include other components used, for example, to guide flexible catheter 4 into the patient—such as, without limitation, a relatively more rigid guide catheter (not shown) or guide wire (not shown).

Flexible catheter 4 includes an elongate, flexible hollow catheter shaft 10 connected to handle 6 at or near a proximal or rear end of the catheter shaft (not shown because it is hidden by a connector at the front end of handle 6), and an electrode assembly 12 disposed at or near a distal or front end 14 of flexible hollow catheter shaft 10. Electrode assembly 12 includes proximal end 13 and distal end 15. It is understood, however, that electrode assembly 12 may be disposed anywhere along flexible hollow catheter shaft 10 intermediate the proximal end and the distal end 14 thereof without departing from the scope of this disclosure. As used herein, the terms proximal and front, and distal and rear, are used with reference to the orientation of catheter system 2 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to handle 6 while the terms distal and front refer to a longitudinal position that is relatively farther from handle 6.

Illustrated electrode assembly 12 is in the form of what may be referred to as an electrode basket and includes struts 20, and is suitably configurable between a collapsed configuration (FIG. 1) for maneuvering and positioning the electrode assembly in the patient, and an expanded configuration (FIG. 2) for operation of the electrode assembly to perform a desired procedure such as an ablation procedure. An annular (e.g., ring-shaped) actuator 16 is mounted on handle 6 for rotation relative thereto and is operatively connected to electrode assembly 12 for selectively configuring the electrode assembly between its collapsed and expanded configurations. It is understood that another suitable actuator (e.g., slide, push button, lever, etc.) may be used instead of rotating actuator 16 to selectively configure electrode assembly 12 without departing from the scope of this disclosure. In some embodiments, electrode assembly 12 may be selectively adjustable between an infinite number of configurations (e.g., degrees of expansion) between its collapsed and expanded configurations using actuator 16.

A control line, such as a suitable cable or pull wire 18 extends from electrode assembly 12 within flexible hollow catheter shaft 10 and into handle 6 for operative connection with the actuator to thereby operatively connect actuator 16 with electrode assembly 12. In some embodiments two or more pull wires, cables or other suitable control lines or tubes may be used for selectively configuring electrode assembly 12. It is also understood that control line 18 may be any suitable control line other than a pull wire, such as a cable, string, tie, compression member or other suitable control to operatively connect electrode assembly 12 to actuator 16. A suitable twisted electrical wire bundle (not shown) also extends through flexible hollow catheter shaft 10 from handle 6 to electrode assembly 12 to deliver power to electrode assembly 12.

As noted above, the present disclosure includes an ablation catheter that is capable of assuming a helical configuration on at least a portion of a distal end of the ablation catheter inside of a blood vessel upon the tensioning of a pull wire connected to a pull ring on a distal end of the catheter. As used herein, the terms "helical" or "helix" refer to a spiral configuration. The helical ablation catheter is inserted into the body in a generally linear configuration, and is transformed into a helical configuration prior to ablation as described herein such that electrodes located on the exterior of the helical ablation catheter can contact the wall of a blood vessel and ablate tissue. The helical ablation catheter can be used with many different types of ablation systems, and may provide for a direct replacement of conventional electrode baskets as described above. In many embodiments, the helical ablation catheter may be connected to a flexible hollow catheter shaft as described above and any electrical wiring, along with the pull wire, routed back to the catheter handle.

Figure 3:
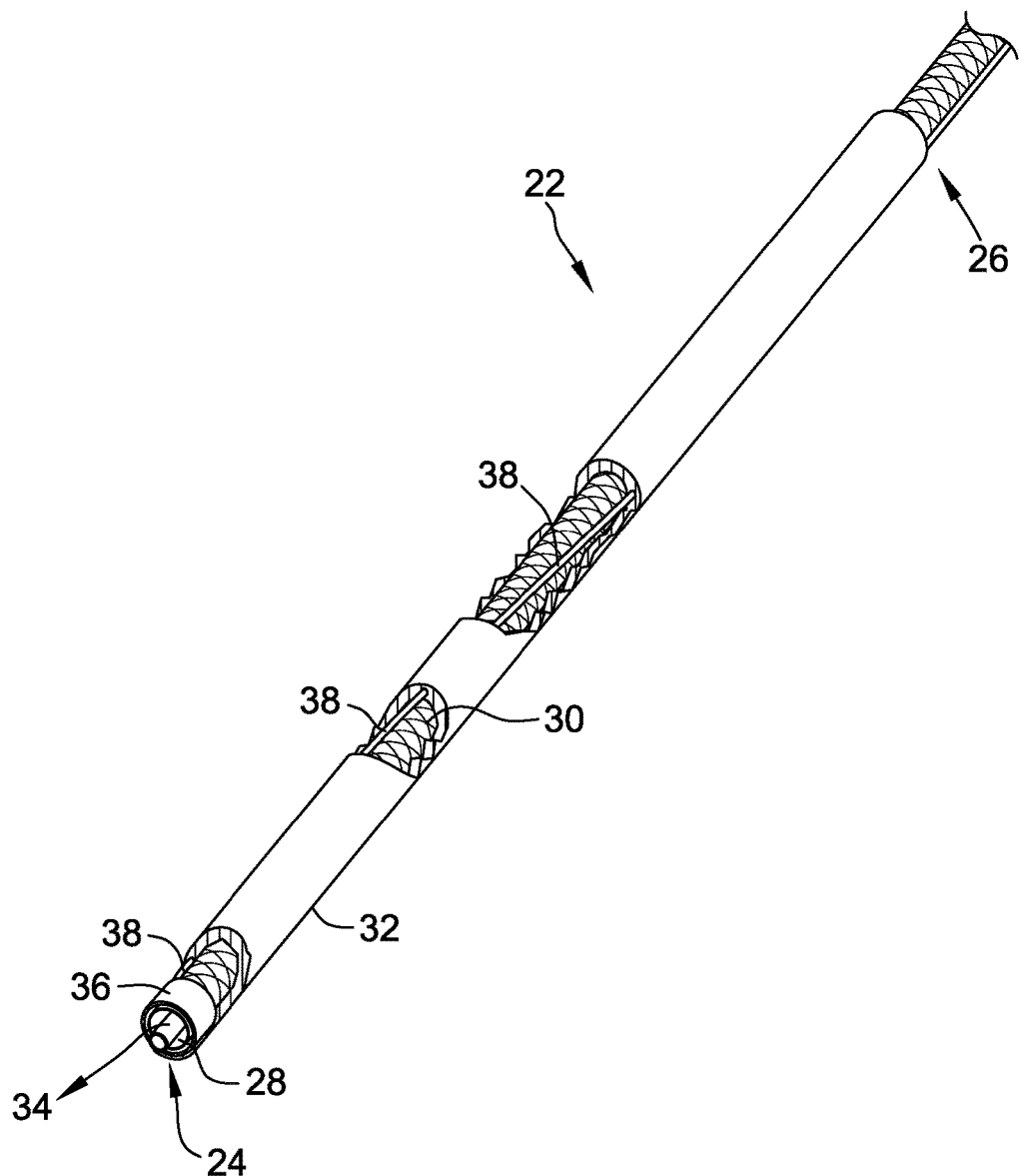
FIG. 3 is a helical ablation catheter of the present disclosure with portions cut away to reveal internal construction.
Figure 4:
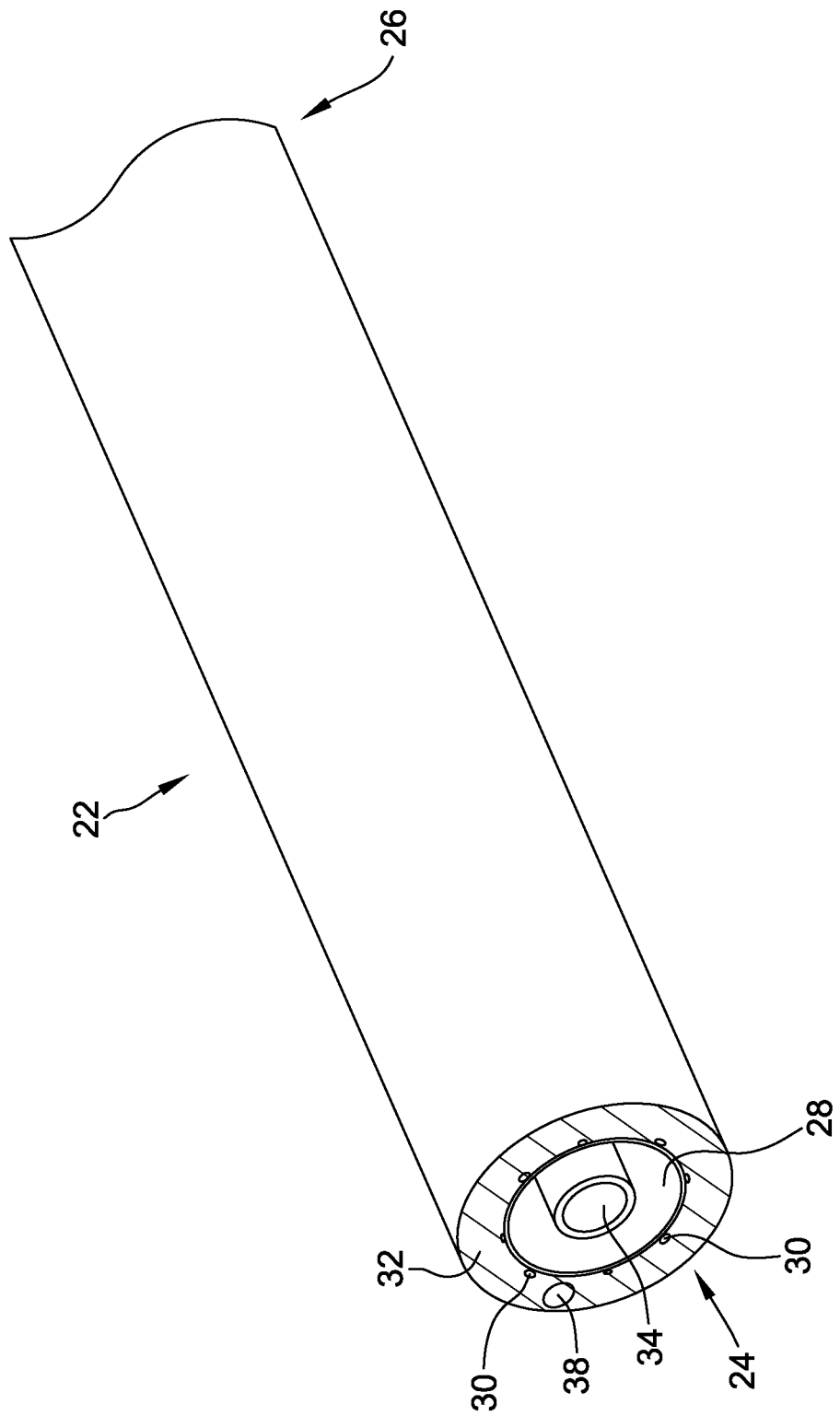
FIG. 4 is a helical ablation catheter of the present disclosure shown in partial cross section.

Referring again to the drawings and specifically to FIG. 3, which illustrates a helical ablation catheter of the present disclosure with portions cut away to reveal internal construction, and FIG. 4, which is an ablation catheter of the present disclosure shown in partial cross section, there is shown helical ablation catheter 22 having distal end 24 and proximal end 26. Helical ablation catheter 22 further includes central lumen 28, middle layer 30, outer jacket 32, guide wire lumen 34, pull ring 36, and pull wire 38. Central lumen 28 contains guide wire lumen 34, which may include a guide wire (not shown) for directing helical ablation catheter 22 to a desired target area inside of a body. Central lumen 28 may be constructed of any material suitable, and such materials are well known to those of ordinary skill in the art. Central lumen 28 may have any desired inner diameter and outer diameter suitable for a particular embodiment. For example, in one embodiment, central lumen 28 may be constructed of a thin layer of polytetrafluoroethylene (PTFE) or similar material, and may have an inner diameter of about 0.03 inches (about 0.076 centimeters) and an outer diameter of about 0.065 inches (about 0.17 centimeters). In another embodiment, central lumen 28 may be constructed of a thermoplastic material.

Referring again to FIGS. 3 and 4, central lumen 28 is surrounded by middle layer 30. Middle layer 30 provides helical ablation catheter 22 with a spring like resilience and memory property such that helical ablation catheter may undergo conformational changes (i.e., from a linear conformation to a helical conformation and vice versa) as described herein without damaging helical ablation catheter 22. Middle layer 30 may be constructed of any suitable spring-like resilient material, but is generally constructed of a braided or woven metal strand material. The woven metal strands may be a plurality of conventional wire strands that have a predetermined relative orientation between the strands. The metal strands define two sets of essentially parallel generally helical stands, with the strands of one set having a "hand", i.e., a direction of rotation, opposite that of the other set. These helical strands may define a generally tubular metal fabric, known in the metal fabric industry as a tubular braid.

The pitch of the wire strands (i.e., the angle defined between the turns of the wire and the axis of the braid) and the pick of the fabric (i.e., the number of wire crossovers per unit length) may be adjusted as known by those of skill in the art to increase/decrease/optimize the rigidity/strength as desired for a particular application. The wire strands of the metal fabric are desirably formed of a material that is both resilient and that can be heat treated to substantially set a desired shape. Materials that are suitable for this purpose include a cobalt-based low thermal expansion alloy referred to in the field as Elgeloy, nickel-based high temperature high-strength superalloys commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by a molding process (described hereinbelow) when subjected to a predetermined heat treatment.

One class of materials that are desirable is memory-shape alloys. Such alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in the present disclosure is Nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." These metal alloys have high elasticity. Nitinol is a particularly desirable alloy for forming middle layer 30.

The metal wires used to fabricate middle layer 30 may include wires having a diameter of from about 0.002 to about 0.005 inches (about 0.051 to about 0.127 millimeters), desirably in the range of from about 0.003 to about 0.0035 inches (about 0.076 to about 0.089 millimeters), and in some embodiments, about 0.003 inches (about 0.076 millimeters). The number of wires in a wire mesh fabric (or tubular braid) may vary from about 36 to about 144, desirably from about 72 to about 144, and in some embodiments, 144. The pick count of the wire mesh may vary from about 30 to about 100, including from about 50 to about 80, including 70. As noted, the wire diameter and the number of wires in the wire mesh fabric will tend to influence the rigidity, strength, and flexibility of middle layer 30. In some embodiments, the metal fabric may be a bioabsorbable metal fabric.

Referring again to FIGS. 3 and 4, outer jacket 32 surrounds middle layer 30, central lumen 28 and guide wire lumen 34 and provides electrical insulation for helical ablation catheter 22. Outer jacket 32 is constructed of a thin layer of an insulting material as is known in the art and, in many embodiments, may be constructed of a suitable thermoplastic or thermoplastic-based material. The thickness of outer jacket 32 may be any suitable thickness known in the art, including for example, about 0.010 inches (about 0.03 centimeters). Outer jacket 32 additionally includes pull wire 38 that is connected to the catheter handle (described above and not shown in FIG. 3 or 4) or other catheter part and pull ring 36 such that when pull wire 38 is tensioned by the catheter handle (or other catheter part) and pulls pull ring 36 toward the catheter handle, a portion of distal end 24 of helical ablation catheter 22 changes from a linear conformation to a helical conformation as described herein. Additionally, helical ablation catheter 22 can be returned to a linear conformation again by releasing the tension on pull wire 38.

Pull wire 38, which may be constructed from a conventional wire material as is well known in the art, is reflowed during the manufacturing process into outer jacket 32 (i.e., continually attached to outer jacket 32) as shown in FIGS. 3 and 4 such that it is contained within outer jacket 32 and connects with pull ring 36, which is also covered and insulated by outer jacket 32. By reflowing pull wire 38 in outer jacket 32 of helical ablation catheter 22, pull wire 38, when tensioned, causes a conformational change of distal end 24 of helical ablation catheter 22 from a linear conformation to a helical conformation. Pull wire 38 is attached to pull ring 36 and extends circumferentially around at least a portion of distal end 24 of helical ablation catheter 22 such that a first end of pull wire 38 (which is connected to pull ring 36) and a second end of pull wire 38 (connected generally to a catheter handle or other tensioning device in the catheter system) are circumferentially spaced apart by a distance of at least 90 degrees, or even at least 120 degrees, or even at least 150 degrees, or even at least 180 degrees. In many embodiments, the circumferential spacing will be about 180 degrees. With this circumferential spacing between the first end and the second end of pull wire 38, when pull wire 38 is tensioned, distal end of 24 helical ablation catheter 22 changes from a linear conformation and assumes a helical conformation. In many embodiments, pull wire 38 is circumferentially spaced about distal end 24 of helical ablation catheter 22 such that, upon tensioning of pull wire 38, a helical conformation of about 0.5 inches (about 1.27 centimeters), or even about 1.0 inches (about 2.54 centimeters), or even about 1.5 inches (about 3.81 centimeters), or even about 2.0 inches (about 5.08 centimeters), or even about 2.5 inches (about 6.35 centimeters) is formed on distal end 24 of helical ablation catheter 22 such that the electrodes can contact tissue during an ablation procedure. In other embodiments of the present disclosure, pull wire 38 may be located between central lumen 28 and middle layer 30 (not shown in the Figures) to provide pull wire 38 with additional strength and rigidity.

Figure 5:
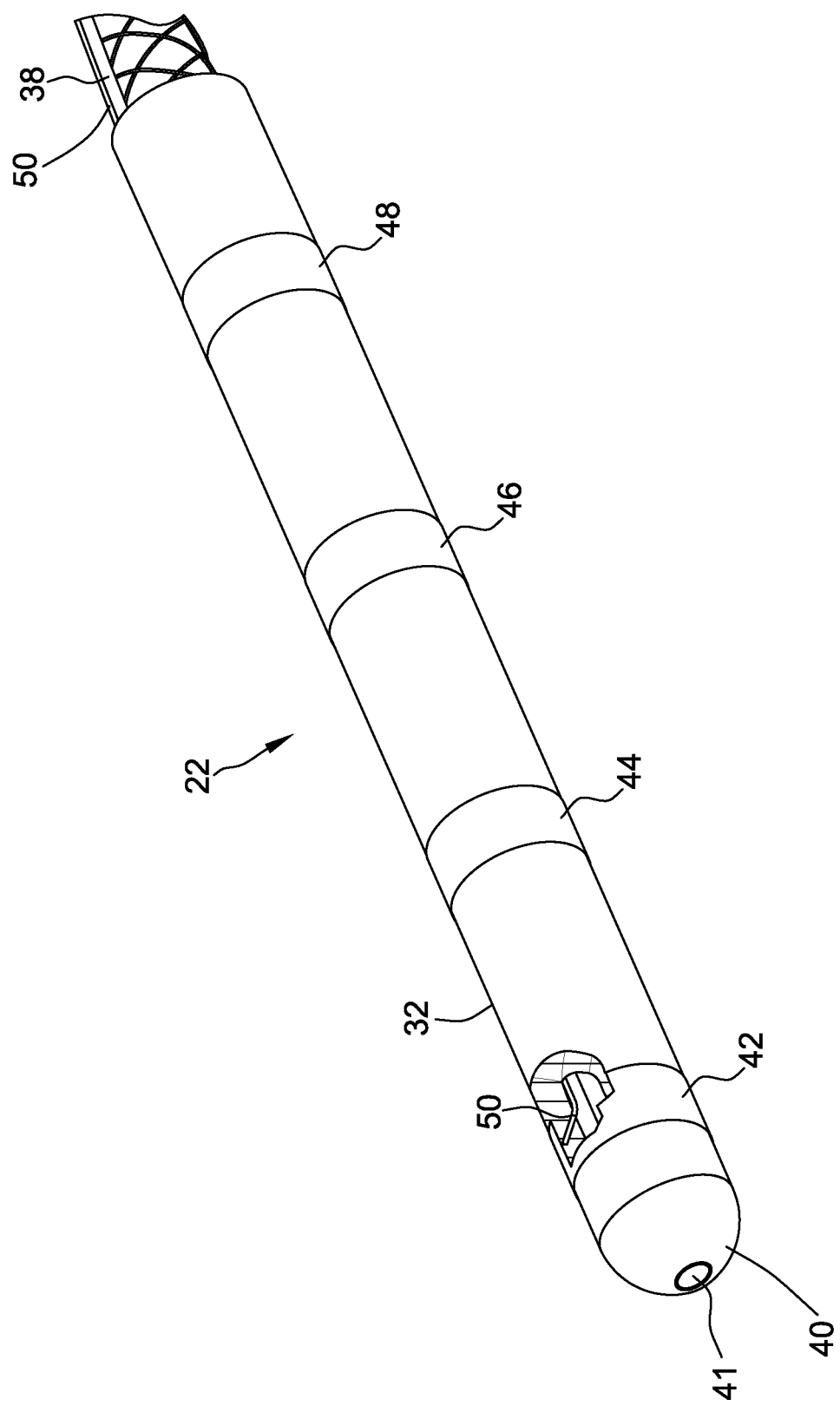
FIG. 5 is a helical ablation catheter of the present disclosure with portions cut away to reveal internal construction.

Referring now to FIG. 5, helical ablation catheter 22 further includes distal tip 40, including distal tip opening 41 (for allowing a guide wire to pass therethrough) and electrodes 42, 44, 46, and 48. Although illustrated in FIG. 5 with a total of four electrodes, helical ablation catheter 22 may include more or less than a total of four electrodes depending upon the intended use and specific application of helical ablation catheter 22. Helical ablation catheter 22 in many embodiments may utilize electrodes that have a larger surface area than electrodes used with conventional ablation catheters. Many conventional ablation catheters typically utilize 2.5 French or 3 French sized electrodes. The helical ablation catheters of the present disclosure, because of their linear conformation for insertion into the body, are more compact and can accommodate larger electrodes, including a 5 French electrode, a 6 French electrode or larger electrodes. As noted above, by using larger electrodes on the helical ablation catheter, the current density applied to the tissue being ablated may be reduced as the energy from the electrodes may be spaced out over a larger area of the vessel, which allows the tissue to better absorb the energy. By spreading the current density over a larger area of the artery, procedural outcomes may be improved and procedure times may be shortened.

Referring again to FIG. 5, helical ablation catheter 22 includes electrical wiring 50 connected to electrode 42 to provide power to electrode 42 during an ablation procedure. Each electrode on helical ablation catheter 22 will include such electrical wiring to power the electrode during a procedure. In many embodiments, electrical wiring 50 will be routed through central lumen 28 (not shown in FIG. 5), through middle layer 30 (not shown in FIG. 5) and outer jacket 32 to electrode 42. Electrical wiring 50 may be routed to a catheter handle described above and ultimately to a power source. Other electrical components, such as sensors, thermocouples, and the like may also be included on helical ablation catheter 22 without departing from the scope of the present disclosure.

In accordance with the present disclosure and as noted herein, the helical ablation catheter is configured such that it may be inserted into a body and into a blood vessel in a linear configuration, which allows electrodes with a larger surface area to be inserted and provide numerous benefits as outlined above. Once inserted to a target location, the helical ablation catheter is capable of forming a helical structure such that the electrodes may come into contact with the wall of blood vessel for an ablation procedure.

Figure 6:
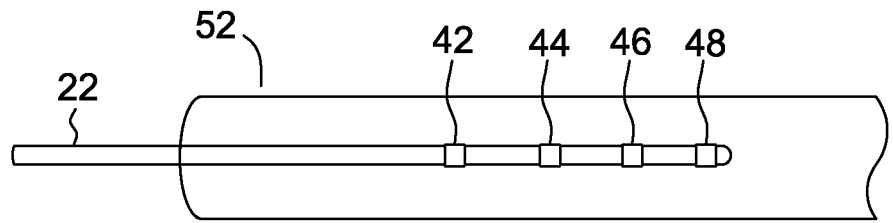
FIG. 6 is a helical ablation catheter of the present disclosure shown in its linear conformation.
Figure 7:
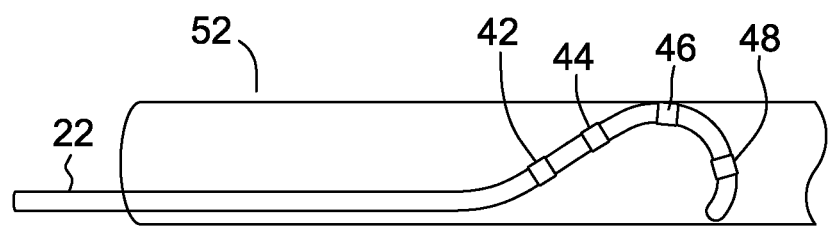
FIG. 7 is a helical ablation catheter of the present disclosure shown in its helical conformation.

Referring now to FIG. 6, there is shown helical ablation catheter 22 including electrodes 42, 44, 46, and 48 inserted into vessel 52 wherein helical ablation catheter 22 is in its linear conformation. FIG. 7 shows helical ablation catheter 22 including electrode 42, 44, 46, and 48 inserted into vessel 52 wherein helical ablation catheter 22 is in its helical conformation such that the electrodes may contact vessel 52.

Helical ablations catheters as disclosed and described herein may suitably be manufactured by one skilled in the art based on the disclosure herein using multiple manufacturing methods and processes. In one exemplary manufacturing method, a helical ablation catheter (similar to that of helical ablation catheter 22 as shown in FIG. 3) is manufactured by first stretching an appropriately sized polytetrafluoroethylene liner over a coated mandrel. Alternatively, a suitable thermoplastic may be reflowed over a Teflon coated mandrel. This polytetrafluoroethylene liner ultimately forms central lumen 28 as shown in FIG. 3. Next, a polytetrafluoroethylene spaghetti tube is stretched over a setup wire to cover the wire for use in a subsequent manufacturing step. The setup wire may, for example, have a diameter of about 0.010 inches (about 0.025 centimeters) and the spaghetti tube may have an inner diameter of about 0.013 inches (about 0.033 centimeters) and a wall thickness of about 0.0015 inches (about 0.0038 centimeters).

A properly sized nitinol braided shaft assembly may then be slid over the polytetrafluoroethylene liner on the mandrel. This braided shaft assembly forms middle layer 30 as shown in FIG. 3. Once the braided shaft assembly is positioned, one end of the setup wire in the spaghetti tube may then be bonded/glued to the distal end of the braided shaft assembly that covers the polytetrafluoroethylene liner on the mandrel. Once the distal end has been bonded/glued to the braided shaft assembly, the setup wire in the spaghetti tube is twisted around the braided shaft assembly until the desired amount of twist (for example, about 180 degrees as illustrated in FIG. 3) has been obtained. At this desired amount of twist, the setup wire in the spaghetti tube is bonded/glued along the length of the braided shaft assembly to the desired length. Suitably, it may be bonded/glued along the length of the braided shaft assembly every 0.1 inches (about 0.25 centimeters) or so.

Once the setup wire in the spaghetti tube has been bonded/glued into place on top of the braided shaft assembly, material (such as a suitable thermoplastic material) that forms the outer jacket (such as outer jacket 32 shown in FIG. 3) is slid over the formed assembly along with a heat shrink material, and the combination is introduced into a suitable reflow oven to reflow the material and form the outer jacket, into which the setup wire in the spaghetti tube is reflowed (as shown in FIG. 3). After this reflowing, the heat shrink material, mandrel, and setup wire are removed.

Next, on the distal end of the catheter (such as distal end 24 as shown in FIG. 3), a pull ring (such as pull ring 36 as shown in FIG. 3) is introduced and a pull wire (such as pull wire 38 as shown in FIG. 3) inserted into the polytetrafluoroethylene spaghetti tube opening formed in the outer jacket during the reflowing process. A tip bonding mandrel is then installed through the pull ring into the distal end of the central lumen formed as described above. Between the pull ring and the tip bond mandrel a thin layer of a thermoplastic material is introduced and slid over the pull ring assembly and covered with a heat shrink material. The assembly is then introduced into a suitable reflow oven and reflowed to form the tip of the helical catheter (such as tip 40 in FIG. 5). After removal from the reflow oven, the heat shrink material is removed along with the mandrel, and the tip of the helical catheter is cut to the desired length.

After cutting the tip to the desired length, holes may be drilled in the desired location(s) for electrode ring wires (such as electrical wiring 50 as shown in FIG. 5) to enter into the central lumen such that it can be appropriately routed to an energy source through the handle. The most proximal electrode ring is slid onto the distal end of the helical catheter and properly positioned and wires run. This is repeated for each desired electrode ring.

As noted above, in some embodiments it may be desirable to locate the pull wire between the central lumen and the middle layer, as opposed to on top of the middle layer prior to forming the outer jacket by reflowing the thermoplastic material. As one skilled in the art will recognize based on the disclosure herein, with this embodiment, the exemplary manufacturing process outlined above may easily be adapted such that the pull wire in the spaghetti tube is bonded onto the polytetrafluoroethylene tube on the mandrel prior to the introduction of the nitinol braided shaft assembly and the subsequent forming of the reflowed outer jacket. Other conformational changes and manufacturing changes are also within the scope of the present disclosure.

In one embodiment of using the helical ablation catheter as described herein, ablation of target tissue in a vessel is accomplished by first inserting a guide wire (not shown in the Figures) into a patient's body (similar to that of vessel 52 shown in FIGS. 6 and 7) and delivering helical ablation catheter 22 in its linear conformation (see FIG. 6) to the target area by advancing helical ablation catheter 22, and specifically guide wire lumen 34, over the guide wire. The guide wire is then removed from at least distal end 24 of helical ablation catheter 22, and pull wire 38 is tensioned via the catheter handle (or other tensioning device in the catheter system) such that distal end 24 of helical ablation catheter 22 forms the helical conformation as shown in FIG. 7. This helical conformation of helical ablation catheter 22 causes electrodes 42, 44, 46, and 48 to contact the tissue to be ablated (or to be in close enough proximity to the tissue to be ablated such that the ablation may occur upon delivering energy to electrodes 42, 44, 46, and 48). Energy is then delivered to electrodes 42, 44, 46, and 48 to conduct the ablation. After the desired ablation of the target tissue is completed (which may include up to 8 or 10 or more ablations), the tension applied to pull wire 38 is released such that helical ablation catheter 22 returns to its original linear conformation (see FIG. 6). Helical ablation catheter 22 may then be moved to a different target area for additional ablations or may be removed from the patient's body.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An ablation catheter comprising:
    a flexible shaft having a proximal end and a distal end;
    a pull wire continuously attached along a portion of a circumference of the distal end of the flexible shaft to a pull ring such that a distal portion of the flexible shaft is configured to form a helical configuration upon tensioning of the pull wire; and
    at least one electrode coupled to the flexible shaft at the distal end.

2. The ablation catheter of claim 1 wherein the pull wire is circumferentially attached to the distal end of the flexible shaft such that a first end of the pull wire and a second end of the pull wire are circumferentially spaced apart by a distance of about 180 degrees.

3. The ablation catheter of claim 1 wherein the at least one electrode comprises at least four electrodes.

4. The ablation catheter of claim 1 wherein the at least one electrode comprises at least six electrodes.

5. The ablation catheter of claim 1 wherein the flexible shaft comprises a central lumen, a middle layer, and an outer jacket.

6. The ablation catheter of claim 5 wherein the central lumen is constructed from polytetrafluoroethylene.

7. The ablation catheter of claim 5 wherein the outer jacket is constructed from a thermoplastic material.

8. The ablation catheter of claim 7 wherein the pull wire is reflowed into the outer jacket.

9. The ablation catheter of claim 5 wherein the middle layer is a braided material.

10. The ablation catheter of claim 9 wherein the braided material is a shape memory alloy.

11. The ablation catheter of claim 1 further comprising a guide wire lumen extending through the central lumen.

12. A method of manufacturing an ablation catheter, the method comprising:
    continuously attaching a pull wire along a portion of a circumference of a distal end of a flexible shaft to a pull ring such that a distal portion of the flexible shaft is configured to form a helical configuration upon tensioning of the pull wire; and
    coupling at least one electrode to the flexible shaft at the distal end.

13. The method of claim 12 wherein continuously attaching the pull wire along the portion of the circumference of the distal end of the flexible shaft comprises circumferentially attaching the pull wire to the distal end of the flexible shaft such that a first end of the pull wire and a second end of the pull wire are circumferentially spaced apart by a distance of about 180 degrees.

14. The method of claim 12 wherein the at least one electrode comprises at least four electrodes, and further comprising coupling the at least four electrodes to the flexible shaft.

15. The method of claim 12 wherein the at least one electrode comprises at least six electrodes, and further comprising coupling the at least six electrodes to the flexible shaft.

16. The method of claim 12 wherein the flexible shaft comprises a central lumen, a middle layer, and an outer jacket.

17. The method of claim 16 wherein the central lumen is constructed from polytetrafluoroethylene.

18. A method of ablating tissue, the method comprising:
    inserting a flexible shaft into a patient wherein the flexible shaft comprises a proximal end and a distal end, a pull wire continuously attached along a portion of a circumference of the distal end of the flexible shaft to a pull ring such that a distal portion of the flexible shaft is configured to form a helical configuration upon tensioning of the pull wire, and at least one electrode coupled to the flexible shaft at the distal end;
    providing tension to the pull wire such that the flexible shaft forms a helical shape; and
    providing energy to the at least one electrode.

* * * * *